US011246699B2

(12) United States Patent
Spindler et al.

(10) Patent No.: US 11,246,699 B2
(45) Date of Patent: Feb. 15, 2022

(54) FLEXIBLE STENT WITH NON-BONDED STENT COVER MATERIAL REGIONS

(71) Applicant: COOK MEDICAL TECHNOLOGIES LLC, Bloomington, IN (US)

(72) Inventors: Ralf Spindler, Solsberry, IN (US); Brent A. Mayle, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 529 days.

(21) Appl. No.: 16/033,408

(22) Filed: Jul. 12, 2018

(65) Prior Publication Data
US 2019/0021840 A1    Jan. 24, 2019

Related U.S. Application Data

(60) Provisional application No. 62/533,928, filed on Jul. 18, 2017.

(51) Int. Cl.
*A61F 2/07* (2013.01)
*A61F 2/90* (2013.01)
(Continued)

(52) U.S. Cl.
CPC ............... *A61F 2/07* (2013.01); *A61F 2/90* (2013.01); *A61F 2/958* (2013.01); *A61F 2/915* (2013.01); *A61F 2002/072* (2013.01); *A61F 2002/075* (2013.01); *A61F 2002/823* (2013.01); *A61F 2002/91575* (2013.01); *A61F 2210/0076* (2013.01); *A61F 2220/005* (2013.01); *A61F 2220/0058* (2013.01); *A61F 2240/001* (2013.01); *A61F 2250/0029* (2013.01)

(58) Field of Classification Search
None
See application file for complete search history.

(56) References Cited

U.S. PATENT DOCUMENTS 6,296,661 B1 * 10/2001 Davila ...................... A61F 2/07
                                                    623/1.13
6,579,314 B1 *  6/2003 Lombardi ................. A61F 2/07
                                                    623/1.13
(Continued)

FOREIGN PATENT DOCUMENTS

WO    WO 2016/183128 A1    11/2016

OTHER PUBLICATIONS

Invitation pursuant to Rule 62a(1) for EP 18275096.8 dated Nov. 21, 2018, 2 pgs.
(Continued)

*Primary Examiner* — Megan Y Wolf
(74) *Attorney, Agent, or Firm* — Crowell & Moring LLP (57) ABSTRACT

A prosthesis is provided for a variety of medical treatments. The prosthesis may include an expandable tubular frame structure and a covering disposed along the frame structure. A proximal liner may be situated along a proximal end of the frame, a distal liner may be situated along a distal end of the frame, and an intermediate liner may be between the proximal liner and the distal liner along the frame. The intermediate liner comprises an extended layer that meets and bonds to the proximal liner and the distal liner at their respective ends. A method of manufacturing the prosthesis is also provided.

14 Claims, 4 Drawing Sheets

(51) Int. Cl.
*A61F 2/958* (2013.01)
*A61F 2/82* (2013.01)
*A61F 2/915* (2013.01)

(56) References Cited

U.S. PATENT DOCUMENTS

| | | |
|---|---|---|
| 7,186,263 B2 | 3/2007 | Golds et al. |
| 7,354,449 B2 | 4/2008 | Goodwin et al. |
| 7,857,843 B2 | 12/2010 | Henderson |
| 8,025,693 B2 | 9/2011 | Quigley |
| 8,034,096 B2 | 10/2011 | Hunt |
| 8,062,346 B2 | 11/2011 | Quigley et al. |
| 8,323,328 B2 | 12/2012 | Martin et al. |
| 8,591,782 B2 | 11/2013 | Nakayama et al. |
| 2003/0074049 A1* | 4/2003 | Hoganson ............... A61F 2/07 623/1.13 |
| 2007/0208409 A1 | 9/2007 | Quigley |
| 2007/0219622 A1 | 9/2007 | Kuppurathanam |
| 2013/0261734 A1 | 10/2013 | Young et al. |
| 2014/0358216 A1 | 12/2014 | Schreck et al. |
| 2017/0035548 A1 | 2/2017 | Bebb et al. |
| 2017/0151051 A1 | 6/2017 | Kang et al. |

OTHER PUBLICATIONS

Extended European Search Report for EP 18275096.8 dated Jan. 22, 2019, 8 pgs.

\* cited by examiner

FLEXIBLE STENT WITH NON-BONDED STENT COVER MATERIAL REGIONS

PRIORITY CLAIM

This invention claims the benefit of priority of U.S. Provisional Application Ser. No. 62/533,928, entitled "Flexible Stent with Non-Bonded Stent Cover Material Regions," filed Jul. 18, 2017, the disclosure of which is hereby incorporated by reference in its entirety.

BACKGROUND

The present disclosure relates to medical devices, in particular to stent grafts, and methods for the manufacture and use of the same for, for example, repair of damaged vessels, ducts, or other physiological pathways.

Various interventions have been provided for weakened, aneurysmal, dissected or ruptured vessels, including surgical interventions and endovascular interventions. Endovascular interventions generally include inserting an endoluminal device or prosthesis such as a stent or stent graft into the damaged or diseased body lumen to provide support for the lumen, and to exclude damaged portions thereof. Such prosthetic devices are typically positioned at the point of treatment or target site by navigation through the vessel, and possibly other connected branch vessels, until the point of treatment is reached. This navigation may require the device to be able to move axially through the vessel(s) prior to deployment, while still maintaining the ability to exert an outward force on the interior wall once deployed.

In the field of aortic interventions, endoluminal devices are placed in vessels to address and correct diseased tissue resulting from atherosclerotic plaques, aneurysm or weakening of body vessel walls, and arterial dissection. In the case of atherosclerosis, plaque buildup results in narrowing of the vessel which may lead to reduced or blocked blood flow within the body vessel. Endoluminal devices for atherosclerosis may act to radially expand the narrowed area of the body vessel to restore normal blood flow. In the case of an aneurysm, a weakening of the body vessel wall results in ballooning of the body vessel which can eventually lead to rupture and subsequent blood loss. In some cases, the aneurysmal sac may include plaque. Endoluminal devices for aneurysms may act to seal off the weakened area of the body vessel to reduce the likelihood of the body vessel rupture. In the case of arterial dissection, a section of the innermost layer of the arterial wall is torn or damaged, allowing blood to enter false lumen divided by the flap between the inner and outer layers of the body vessel.

Such endoluminal devices are placed in the vasculature that is in high motion and, in some cases, a flexible environment. A device with low flexibility may cause restenosis or vessel dissection. Furthermore, advancements in graft materials to improve interaction with the stent frame have been developed, including increasing the thickness of the graft material and/or including reinforcements within the graft materials. What is needed is an improved implantable prosthesis device construct.

SUMMARY

In a first embodiment, a prosthesis comprises an expandable tubular frame structure having a proximal frame end and a distal frame end. A covering is disposed along the frame structure, the covering including a first liner, a proximal liner, and a distal liner discrete from the proximal liner. The first liner comprises a plurality of first liner layers, wherein at least one of the first liner layers is an extended layer extending beyond a proximal end of the remaining first liner layers and a distal end of the remaining first liner layers of the first liner. A proximal end of the extended layer is bonded to the proximal liner along the proximal frame end at a first coupling segment, and a distal end of the extended layer is bonded to the distal liner along the distal frame end at a second coupling segment. One of the first liner layers immediately adjacent to the expandable tubular frame structure remains unbonded to the expandable tubular frame structure along an intermediate region of the frame structure disposed between the proximal and distal frame ends.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Medical devices for implantation within a human or animal body for repair of damaged vessels, ducts, or other physiological pathways are provided. Such medical devices may be constructed in a manner to reduce the graft material thickness, increase the device flexibility, and/or reduce the delivery profile. In the present application, the term "proximal end" is used when referring to that end of a medical device closest to the heart after placement in the human body of the patient, and may also be referred to as inflow end (the end that receives fluid first), and the term "distal end" is used when referring to that end opposite the proximal end, or the one farther from the heart after its placement, and may also be referred to as the outflow end (that end from which fluid exits).

A medical device may be any device that is introduced temporarily or permanently into the body for the prophylaxis or therapy of a medical condition. For example, such medical devices may include, but are not limited to endovascular grafts, stents, stent grafts, bifurcated stent grafts or assembly of a multicomponent prosthesis, balloon catheters, meshes, vascular grafts, stent-graft composites, filters (for example, vena cava filters), vascular implants, tissue scaffolds, myocardial plugs, valves (for example, venous valves), various types of dressings, endoluminal prostheses, vascular supports, or other known biocompatible devices.

Regardless of its configuration, the medical device may have a reduced diameter delivery state in which the medical device may be advanced to a target location within a vessel, duct, or other anatomical site. The medical device may further have an expanded deployed state in order to apply a radially outward force upon the vessel, duct, or other anatomical site. In the expanded state, fluid flow is allowed through a central lumen of the medical device.

Figure 1:
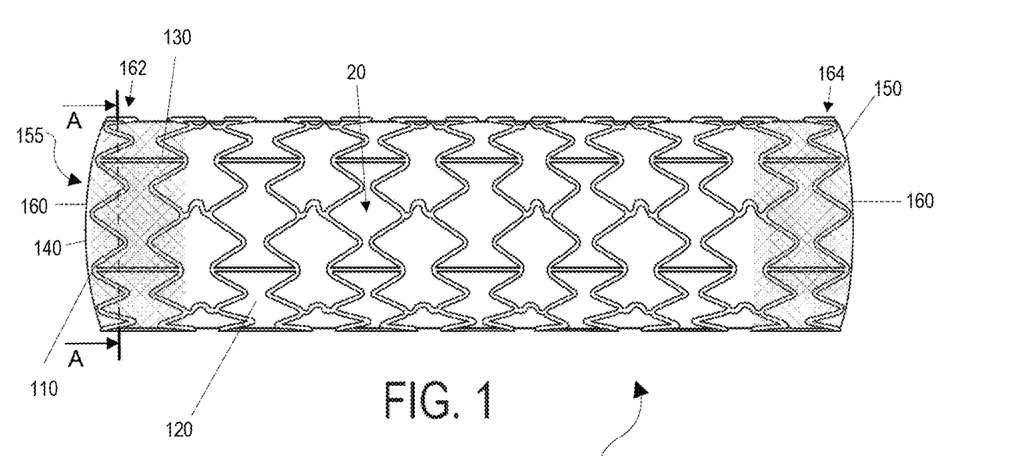
FIG. 1 is a side view of an example of a stent-graft.

Now looking more closely at the drawings, FIG. 1 depicts one example of a medical device (shown as a stent-graft 100), including a tubular stent frame 110 and a graft coverings 120 disposed along the stent frame 110. The stent-graft 100 may be cylindrical along the entire length of the stent frame 110. It is contemplated the stent-graft 100 may have segments that are tapered. In one example, the stent-graft 100 is suitable for placement into an aorta and engaging against the aorta. The stent-graft 100 may comprise a proximal end 140 and a distal end 150, and includes a lumen 155 extending about a longitudinal axis 160. The stent-graft 100 includes a luminal side 170 facing the lumen 155 and an abluminal side 172 opposite the luminal side 170. The stent frame 110 may be balloon expandable or self-expanding.

The stent frame 110 may include a single integrated stent frame structure along the length of the stent-graft or may include a plurality of discrete stent ring members, some of which may be interconnected. In one example, the stent frame 110 may include a longitudinal strut 130 interconnecting adjacent stent ring members. A plurality of longitudinal struts may be circumferentially disposed relative to another. In one example, the stent-graft 100 may be configured without the longitudinal struts 130. The longitudinal struts 130 may be oriented in a longitudinal direction along the longitudinal axis 160, or at some different angle. Portions of the stent frame 110 may be spaced, for example, to define open and/or closed cells or interstices 20. The graft covering 120 may form a liner sheet to keep fluid in the stent-graft 100 after implanting the stent-graft 100 into a patient. As will be described, the graft covering 120 may include a proximal graft segment 162 and a distal graft segment 164 discrete from one another (as shown by the shaded regions).

Figure 2:
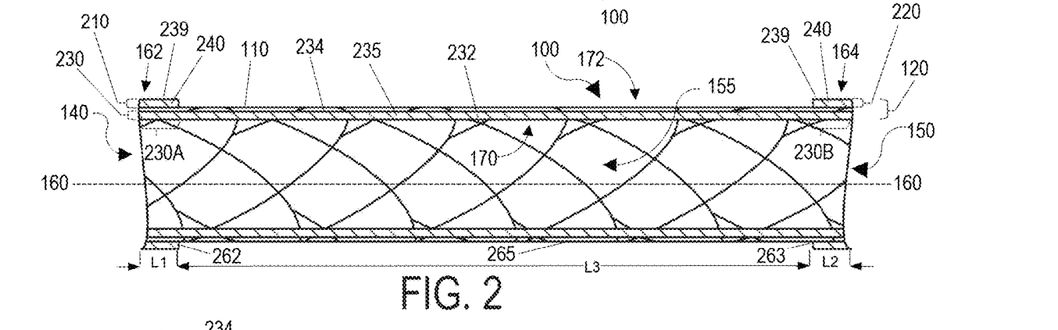
FIG. 2 is an axial cross-sectional view of the stent-graft in FIG. 1.

FIG. 2 is an axial cross-sectional view of a stent-graft 100 wherein the proximal graft segment 162 of the graft covering 120 includes a proximal liner 210 disposed along the stent frame 110 and positioned at the proximal end 140 of the stent-graft 100, the distal graft segment 164 includes a distal liner 220 disposed along the stent frame 110 and positioned at the distal end 150 of the stent-graft 100, and a first liner 230 disposed along the stent frame 110 between the distal end 150 and the proximal end 140. In one example, the first liner 230 is disposed within the lumen 155 along the luminal side 170 of the stent frame 110, and the proximal and distal liners 210, 220 are disposed along the stent frame 110 exterior to the lumen 155 along the abluminal side 172. Alternatively, the first liner 230 may be an outer liner disposed along the stent frame 110 exterior to the lumen 155, and the proximal and distal liners 210, 220 are disposed along the luminal side 170 of the stent frame 110. A proximal segment 230A of the first liner 230 is configured to be bonded to the proximal liner 210, and a distal segment 230B of the first liner 230 is configured to be bonded to the distal liner 220. As will be described, at least a portion of a segment of the first inner liner 230 disposed between the proximal segment 230A and the distal segment 230B remains unbonded to the stent frame 110. Because of this unbonded intermediate region, the stent-graft 100 may obtain higher longitudinal flexibility than this same region being bonded to the graft covering. The freedom of movement of the stent frame 110 and the graft covering 120 independent from one another along the unbonded intermediate region may result in a highly flexible stent-graft 100 suitable for highly tortuous body vessels or for high motion body vessels, which may reduce the risk of restenosis and vessel dissections along these body vessels.

The first liner 230 may include one or more first liner layers. In one example, the first liner 230 may include a first first liner layer 232, a second first liner layer 234, and a third first liner layer 235. The layers 232, 234 may provide structural support, blood compatible surfaces, and/or resistance to permeability. The one layer of the layers 232, 234 immediately adjacent (that is, in closest proximity to) the stent frame 110 may be configured to remain unbonded to the stent frame 110. The third first liner layer 235 may be configured for bonding the layers 232, 234 and/or to the stent frame 110. The third first liner layer 235 may be disposed between the layers 232, 234.

The proximal and/or distal liners 210, 220 may include one or more liner layers. In one example, each of the liners 210, 220 may include a support layer 239 and a bonding layer 240. The support layer 239 may provide structural support, blood compatible surfaces, and/or resistance to permeability. The bonding layer 240 is disposed immediately adjacent to the stent frame 110 and may be configured for bonding to the immediately adjacent one of the layers 232, 234 and/or to the stent frame 110.

FIG. 2 shows the bonding layer 240 of the proximal liner 210 may be disposed between the segment of the second first liner layer 234 associated with the proximal segment 230A. The bonding layer 240 of the distal liner 220 may be disposed between the segment of the first first liner layer 232 associated with the distal segment 230B. The first liner 230 may be bonded to the proximal liner 210 and to the distal liner 220 through the respective bonding layers 240, and the first liner 230 may remain unbonded to at least a portion of the stent frame 110. The proximal liner 210 and the distal liner 220 each have longitudinal lengths, L1 and L2, respectively. The length of stent-graft 100 disposed between the respective inner edges 262, 263 of the proximal and distal liners 210, 220 define an intermediate section 265 having a longitudinal length L3. It is along at least a portion of the intermediate section 265 that the first liner 230 remains unbonded to the stent frame 110.

The bonding layer 240 at each of the proximal end 140 and the distal end 150, and the third first liner layer 235 may comprise the same or different materials in relation to each other. In some examples, the bonding layer 240 and the third first liner layer 235 may include, in any combination in relation to each other: strips of material, adhesives, crimping, or suture yarn, or any combination thereof. Some examples of suitable adhesives may be medical glue or super glue while some examples of suitable suture yarn material may be PET.

Figure 3:
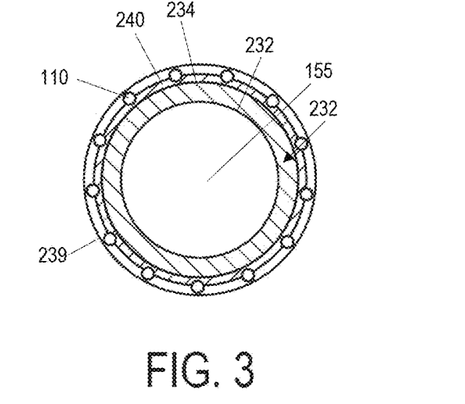
FIG. 3 is a radial cross-sectional view of the stent-graft in FIG. 1, taken along line A-A, prior to a bonding operation.

FIG. 3 is a radial cross-sectional view of the proximal end 140 of the stent-graft 100 prior to the bonding operation. FIG. 3 shows the multiple layers surrounding the stent frame 110. In one example, the lumen 155 may be defined by the first liner 230, and the stent frame 110 is disposed between the first liner 230 and the proximal liner 210. The lumen 155 may be defined by one of the first or second first liner layers 232 or 234 of the first liner 230. In one example, the second first liner layer 234 is adjacent to the stent frame 110 and the layer 232 is disposed facing the lumen 155 with the layer 235 disposed therebetween. The bonding layer 240 of the proximal liner may be disposed along the outside of the stent frame 110 and the support layer 239 may be disposed overlapping the bonding layer 240. In one example, the bonding layer 240 may be disposed over the layer 234 underneath the stent frame 110 with the support layer 239 disposed along the outside of the stent frame 110.

An adhesive, threading, or other attachment means may be used to temporarily fix the relative locations of any of the layers prior to heating. The third first liner layer 235 and/or the bonding layer 240 may melt when subjected to a melt temperature and solidify upon cooling. The heat received by the layers may cause material of the layers to melt and form around the struts of the stent frame 110. After cooling, the layers may solidify to occupy a substantial amount of the space between the proximal and distal liners 210, 220 and the corresponding proximal and distal segments 230A, 230B associated with the first liner 230 to form the proximal graft segment 162 as a first proximal coupling site (for example, bonding site) and the distal graft segment 164 as a second distal coupling site (for example, bonding site), respectively.

Figure 4:
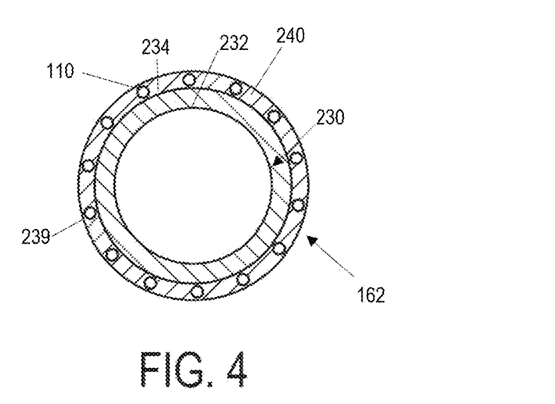
FIG. 4 is a radial cross-sectional view of the stent-graft in FIG. 1, taken along line A-A, subsequent to a bonding operation.

FIG. 4 is a radial cross-sectional view of the proximal end 140 of the stent-graft 100 shown in FIG. 2 after the bonding operation. The proximal liner 210 is bonded to the first liner 230 via the bonding layer 240 through the closed cells or interstices 20 of the stent frame 110 to define the proximal graft segment 162. Although not shown in FIG. 4, the distal liner 220 is bonded to the first inner liner 230 through the closed cells or interstices 20 of the stent frame 110 to define the distal graft segment 164. To this end, the stent-graft 100 may be constructed in a manner to reduce the total graft material wall thickness along the intermediate of the graft covering, which may allow for a greater compressed diameter for the stent-graft 100' and reduce its delivery profile.

Figure 5:
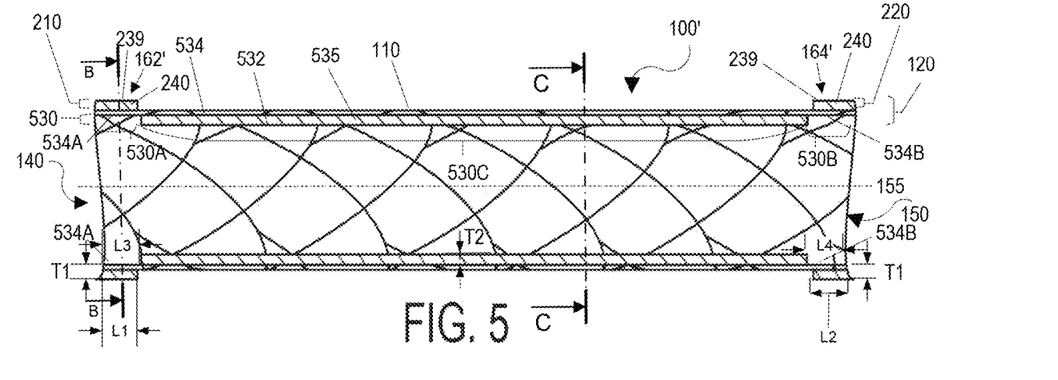
FIG. 5 is an axial cross-sectional view of another example of a stent-graft.

FIG. 5 is an axial cross section of another example of the stent-graft (now referred to as 100'), where similar references used in the description of the stent-graft 100 will be used to describe similar components in the stent-graft 100'. The stent-graft 100' may be constructed to include relatively thinner walled proximal and distal graft segments (now referred to as 162' and 164'). The graft covering 120 of the stent-graft 100' includes another example of the first liner (now referred to as the first liner 530). The second first liner layer 534 of the first liner 530 that is immediately adjacent to the stent frame 110 is shown extending beyond the remaining first liner layers (that is, the first first liner layer 532 and the third first liner layer 535) toward both the proximal end 140 and the distal end 150 of the stent-graft 100'. The proximal extension 534A of the second first liner layer 534 corresponds to the proximal segment 530A of the first liner 530 that is configured to be bonded to the proximal liner 210. The proximal extension 534A extends beyond the remaining layers to the proximal end of the device by a first longitudinal length L3. The distal extension 534B of the second first liner layer 534 corresponds to the distal segment 530B of the first liner 530 that is configured to be bonded to the distal liner 220. The distal extension 534B extends beyond the remaining layers to the distal end of the device by a second longitudinal length L4. As will be described, at least a portion of a segment of the first inner liner 530 disposed between the proximal segment 530A and the distal segment 530B remains unbonded to the stent frame 110. In some examples, the bonding layer 240 of the proximal and distal liners 210, 220 may bond to the proximal and distal extensions 534A, 534B, respectively, of the second first liner layer 534. An intermediate segment 534C of the second first liner layer 534 disposed between the extensions 534A, 534B remains unbonded to the stent frame 110. In one example, the longitudinal length L1 of the proximal liner 210 is substantially the same as the first longitudinal length L3 of the proximal extension 534A, and the longitudinal length L2 of the distal liner is substantially the same as the second longitudinal length L4 of the distal extension.

A first wall thickness T1 of the proximal and/or distal graft segments 162', 164' may be about the same as a second wall thickness T2 of the intermediate segment 534C of the second first liner layer 534. In one example, the proximal and/or distal graft segments 162', 164' have a common wall thickness. FIG. 5 shows the combination of the radial thicknesses of each of the proximal and distal liner 210 (with the support layer 239 and the bonding layer 240) and corresponding proximal and distal extensions 534A, 534B of the second first liner layer 534 may be approximately equivalent to the second wall thickness T2 of the first, second, and third first liner layers 532, 534, 535. The thinner walled proximal and distal graft segments 162', 164' may require less material for manufacture and may result in a lower profile stent-graft when crimped and/or radially compressed. To this end, the stent-graft 100' may be constructed in a manner to reduce the total graft material thickness at the ends of the stent graft to make the thickness comparable to the thickness along the intermediate of the graft covering, which may allow for a greater compressed diameter for the stent-graft 100' to reduce the delivery profile.

In one embodiment, the thicknesses T1 and T2 may be same (or substantially the same) in the crimped state of the stent graft. However, the thicknesses may be designed to be different in the expanded state. For example, when using a more spongy liner material at the proximal and/or distal ends, the liner material at these locations would be slightly thicker compared to liner material in the central region.

Notably, in general, a more flexible liner material on both stent graft ends, compared to liner material in the central region, may be chosen to better match the viscoelastic behavior of the vessel wall. This may reduce the likelihood of turbulent blood flow and thrombus formation.

Figure 6:
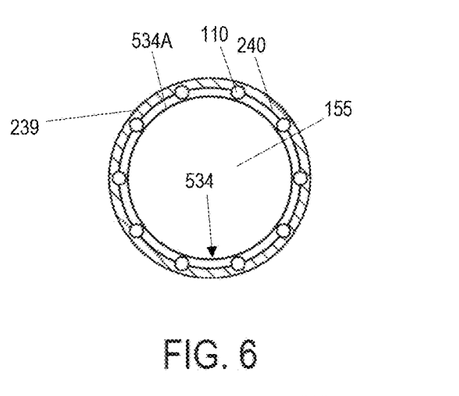
FIG. 6 is a radial cross-sectional view of the stent-graft in FIG. 5, taken along line B-B, prior to a bonding operation.

FIG. 6 is a radial cross-sectional view of a stent-graft 100' in FIG. 5 taken along line B-B before the bonding operation. FIG. 6 shows one example wherein the bonding layer 240 is disposed along the proximal liner 210 prior to a bonding operation to the proximal extension 534A of the second first liner layer 534. For example, the lumen 155 may be defined by, for example, the first liner 530, and the stent frame 110 may be disposed between the first liner 530 and the proximal liner 210. The second first liner layer 534 is shown adjacent to the stent frame 110 and the layer 532 is disposed facing the lumen 155 with the layer 535 disposed therebetween. The bonding layer 240 of the proximal liner is disposed along the outside of the stent frame 110 and the support layer 239 is disposed overlapping the bonding layer 240. In one example, the bonding layer 240 may be disposed over the layer 234 underneath the stent frame 110 with the support layer disposed along the outside of the stent frame 110. Similarly, but not shown, the distal end 150 may comprise a layer similar to the bonding layer 240 that may be similarly disposed at the bonding layer of the proximal liner.

Figure 7:
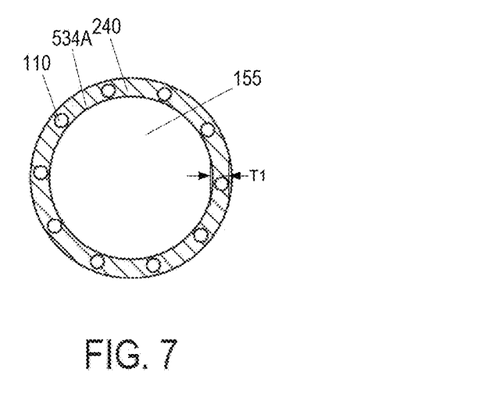
FIG. 7 is a radial cross-sectional view of the stent-graft in FIG. 5, taken along line B-B, subsequent to a bonding operation.

FIG. 7 is a radial cross-sectional view of the proximal end 140 of the stent-graft 100 shown in FIG. 5 taken along line B-B subsequent a bonding operation. As depicted, the proximal extension 534A bonds to the support layer 239 via the bonding layer 240 to define a total first wall thickness T1.

Figure 8:
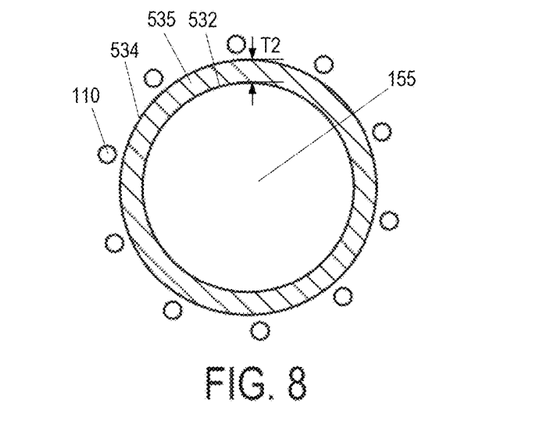
FIG. 8 is a radial cross-sectional view of the stent-graft in FIG. 5, taken along line C-C, subsequent to a bonding operation.

FIG. 8 is a radial cross-sectional view of the first liner 530 of stent-graft 100 taken along line C-C in FIG. 5. The stent frame 110 is radially outward from the first liner 530 and the stent frame 110 remains unbonded to the first liner 530. This unbonded configuration is advantageous to the stent-graft 100 at least by allowing increased flexibility. As depicted, the second first liner layer 534 bonds to the first first liner layer 532 via the bonding of the third first liner layer 535 to define a total second wall thickness T2.

Figure 9:
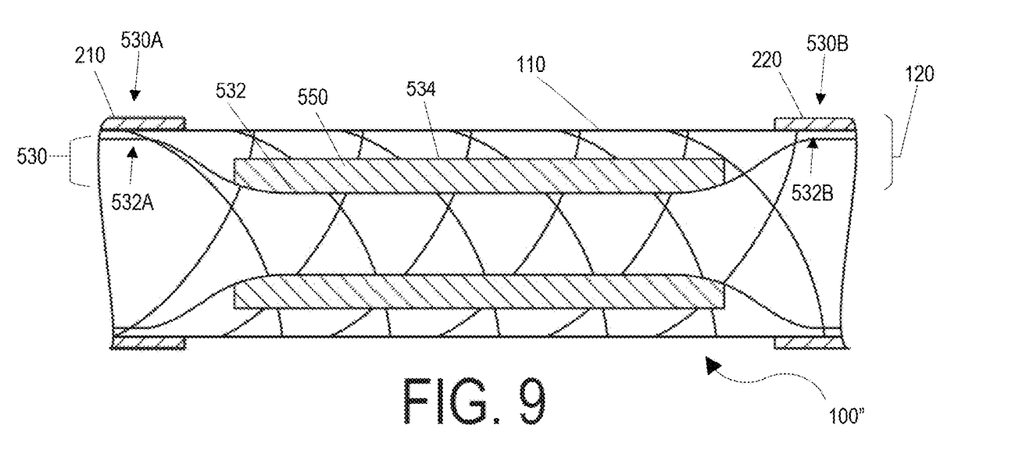
FIG. 9 is an axial cross-sectional view of another example of a stent-graft.

FIG. 9 is an axial cross section of another example of the stent-graft (now referred to as 100"), where similar references used in the description of the stent-graft 100 or 100', will be used to describe similar components in the stent-graft 100". The proximal extension 532A of the first first liner layer 532 corresponds to the proximal segment 530A of the first liner 530 that is configured to be bonded to the proximal liner 210. The distal extension 532B of the first first liner layer 532 corresponds to the distal segment 530B of the first liner 530 that is configured to be bonded to the distal liner 220. The second first liner layer 534 is disposed adjacent to the stent frame 110 and the first first liner layer 532 is bonded to the proximal liner 210 and the distal liner 220 by the proximal and distal extensions 532A, 532B of the first first liner layer 532 that extend beyond the second first liner layer 534. In this configuration, the first first liner layer 532 may exert pressure radially outward on the second first liner layer 534. The second first layer liner 534 defines the unbonded intermediate region of the graft covering. After the bonding operation, the cross-section of the stent graft 100" would appear similar to what is shown in FIGS. 7 and 8.

Figure 10:
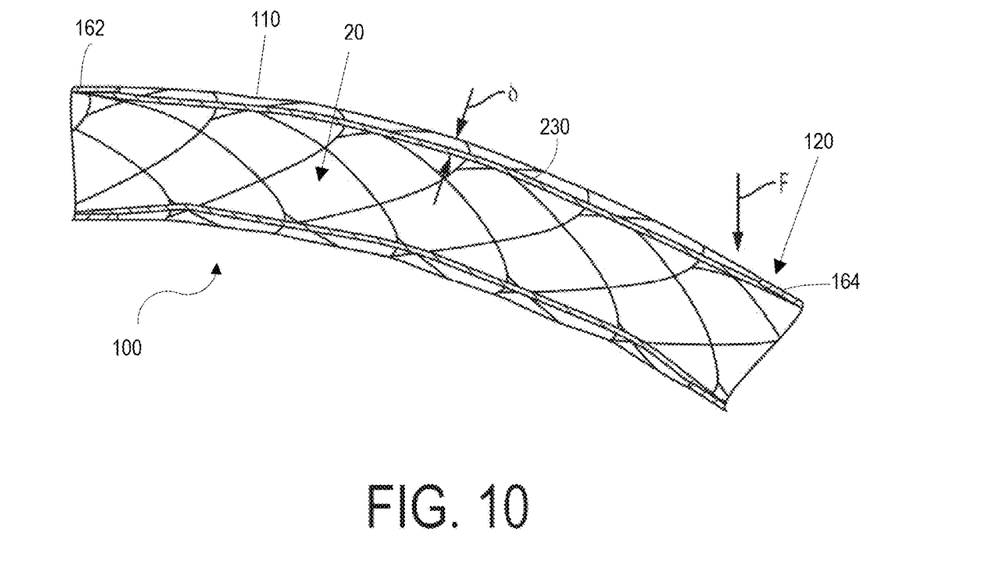
FIG. 10 depicts an example of a stent-graft under a moment load.

FIG. 10 shows an example of a force F applied to the distal end 120 of the stent-graft 100 causing a moment load to the stent-graft. The stent-graft 100 includes the proximal and distal graft segments 162, 164 bonded to the respective ends of the stent frame 110, and the intermediate section of the first liner 230 unbonded to the stent frame 110. As shown, the first liner 230 may further separate from the stent frame 110 by a distance δ during the moment load. Since the intermediate section of the stent frame is unconstrained by the graft material, greater axial and/or longitudinal bending flexibility from the stent-graft may be realized due to the struts of the stent frame having movement independent to the graft. To this end, the stent-graft may have a more suitable flexibility to conform to a high motion or flexible environment in which the stent-graft 100 is situated in a patient.

Although the focus of the description has been on bonding the layer liners together, it is contemplated that other attachment mechanisms may be utilized, with keeping the intermediate segment of the first liner unbonded. The proximal and distal liners may be bonded to any part of the first liner by, for example, tying using strips of material, adhesives, crimping, or suture yarn. Some examples of suitable adhesives may be medical glue or super glue while some examples of suitable suture yarn material may be PET.

The term "stent frame" means any device or structure that provides or is configured to provide rigidity, expansion force, or support to a body part, for example, a diseased, damaged, or otherwise compromised body lumen. The stent frame may include any suitable biocompatible material, including, but not limited to fabrics, metals, plastics, and the like. Examples of suitable materials include metals such as stainless steel, cobalt chrome (CoCr), and nitinol, and plastics such as polyethylene terephthalate ("PET"), polytetrafluoroethylene ("PTFE") and polyurethane. The stent frame may be "expandable," that is, it may be capable of being expanded to a larger-dimension configuration. The stent frame may expand by virtue of its own resilience (i.e., self-expanding), upon the application of an external force (i.e., balloon-expandable), or by a combination of both. In one example, the stent may have one or more self-expanding portions and one or more balloon-expandable portions. The stent struts that are interconnected to one another represent specific configurations of a wire member that comprises a basic structural component of the stent. As used herein, the term "wire" or "strut" refers to any filamentary member, including, but not limited to, drawn wire and filaments that have been laser cut from a cannula.

The stent frames described herein may be associated with the graft covering to form a stent-graft. For example, the stent frame may be coupled along an interior, exterior, or both surface of the graft tubular body by suture attachments, by dipping into a liquefied polymer of graft material that is allowed to cure, by layers of graft sheets that are heated for bonding. The term "graft covering" describes an object, device, or structure that is joined or that is capable of being joined to a body part to enhance, repair, or replace a portion or a function of that body part. Graft coverings can be used to repair body vessels include, for example, films, coatings, or sheets of material that are formed or adapted to conform to the body vessel that is being enhanced, repaired, or replaced. The graft material may include a biocompatible synthetic or biological material. Examples of suitable synthetic materials include fabrics, woven and non-woven materials, and porous and non-porous sheet materials. Other synthetic graft materials include biocompatible materials, which may include nanotubes, such as polyester, polytetrafluoroethylene (PTFE), polyurethane, expanded polytetrafluoroethylene (ePTFE), electrospun polytetrafluoroethylene (esPTFE), polyethylene terephthalate (PET), fluorinated ethylene propylene (FEP), or combinations thereof. Examples of suitable biological materials include, for example, pericardial tissue and extracellular matrix materials such as SIS.

Figure 11:
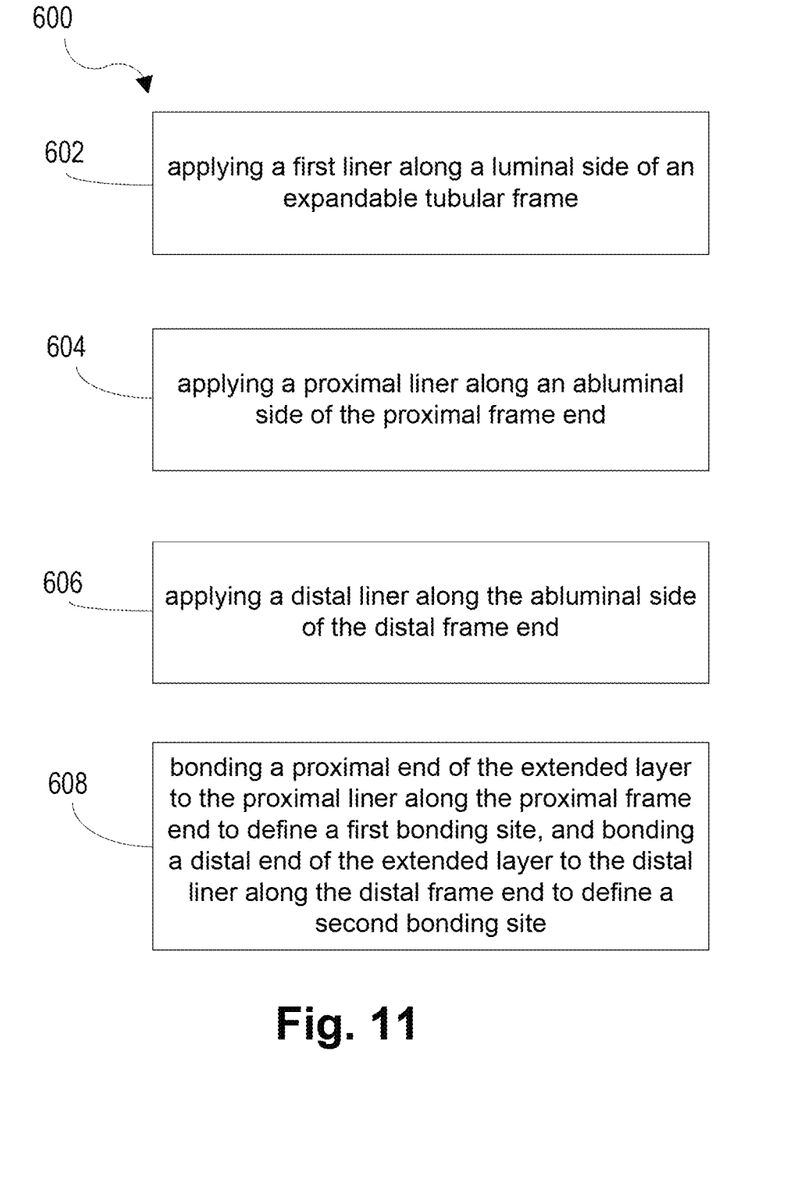
FIG. 11 is a flow diagram depicting a method of making a prosthesis.

FIG. 11 depicts a method 600 of making a prosthesis. In one exemplary method of making a prosthesis, such as any one of the stent-grafts disclosed herein, a first liner is applied along the luminal side of the stent frame (step 602). When the first liner comprises multiple layers, an inner support layer, a bonding layer, and an outer support layer may be applied along a mandrel. In one example, the support layers include PTFE. The stent frame is disposed over the layers of the first liner that are on the mandrel. One of the first liner layers may be an extended layer extending longitudinally beyond both ends of the remaining first liner layers. The bonding layer is configured to bond to the inner and outer support layers. In one example, the bonding layer includes polyurethane. The proximal liner is disposed along the abluminal side of the proximal end of the stent frame (step 604). The distal liner is disposed along the abluminal side of the distal end of the stent frame (step 606). When the proximal and distal liner are multi-layers, the liners include a support layer, such as, for example, PTFE, and a bonding layer, such as for example, polyurethane. The proximal and distal liners are disposed over the stent frame while on the mandrel to define a construct ready for heating. The construct is heated, for example, by an oven, at a suitable time, temperature and pressure for the bonding materials to melt for bonding the proximal end of the extended layer to the proximal liner along the proximal frame end to define the first bonding site, and for bonding the distal end of the extended layer to the distal liner along the distal frame end to define the second bonding site (step 608). During heating, the bonding layer of the first liner melts and attaches to the support layers of the first liner, and the bonding layer of the proximal and distal liners melts and attaches to the struts of the stent frame and to the outer support layer of the first liner. The intermediate region of the frame structure between the proximal and distal frame ends remains unbonded to the first liner. As described above, the first liner and the proximal and distal liners may be placed along the opposite sides than shown. In the case, the proximal and distal liners may be applied along the luminal side for step 602, while the first liner may be applied along the abluminal side for steps 604 and 606. Instead of bonding, the liners may be coupled to one another as described herein.

Methods of using any one of the medical devices described herein, such as by placing a medical device described herein into a body at a point of treatment, such as a point of treatment in an aortic system having an aneurysm. Also, methods of using the medical devices described herein in combination with another medical device, such as by placing a medical device described herein as a branch connecting stent within a fenestrated stent graft, and placing the medical devices together into a body at a point of treatment, such as a point of treatment in the aortic system. The medical device may be delivered with suitable techniques, depending on the type of medical device. In one example, access to the body may be attained by inserting an access device, such as an introducer sheath, into the body passageway. One typical procedure for inserting the introducer sheath over an inserted wire guide using the well-known Seldinger percutaneous entry technique. The medical device may be delivered with a stent deployment system using the introducer sheath, and advanced to the treatment site, such as the aneurysm, typically using visual techniques such as fluoroscopy. The medical device may be radially compressed to a lower profile for delivery. An outer sheath is moved relative to the medical device to allow for radial expansion within the body. Trigger wires may be provided and activated for selective expansion of the medical device. Once implanted, the system may be removed from the body.

To clarify the use of and to hereby provide notice to the public, the phrases "at least one of <A>, <B>, ... and <N>" or "at least one of <A>, <B>, ... <N>, or combinations thereof" or "<A>, <B>, ... and/or <N>" are defined by the Applicant in the broadest sense, superseding any other implied definitions hereinbefore or hereinafter unless expressly asserted by the Applicant to the contrary, to mean one or more elements selected from the group comprising A, B, ... and N. In other words, the phrases mean any combination of one or more of the elements A, B, ... or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis comprising:
    an expandable tubular frame structure having a proximal frame end and a distal frame end;
    a covering disposed along the frame structure, the covering including a first liner, a proximal liner, and a distal liner discrete from the proximal liner, the first liner comprising a plurality of first liner layers, wherein at least one of the first liner layers is an extended layer extending beyond a proximal end of remaining first liner layers and a distal end of the remaining first liner layers of the first liner,
    wherein the extended layer comprises an extended liner layer proximal end, an extended liner layer distal end, and an intermediate segment disposed between the extended liner layer proximal and distal ends;
    wherein the extended liner layer proximal end is bonded to the proximal liner along the proximal frame end at a first coupling segment, and the extended liner layer distal end is bonded to the distal liner along the distal frame end at a second coupling segment,
    wherein a non-extended liner layer of one of the remaining first liner layers fails to overlap with the proximal and distal liners, and
    wherein one of the first liner layers immediately adjacent to the expandable tubular frame structure remains unbonded to the expandable tubular frame structure along an intermediate region of the frame structure disposed between the proximal and distal frame ends.

2. The prosthesis of claim 1, wherein the first and second coupling segments have a common wall thickness, and an intermediate segment of the first liner that remains unbonded to the expandable tubular frame structure comprises a wall thickness sized the same as the common wall thickness.

3. The prosthesis of claim 1, wherein the extended liner layer proximal end comprises a first longitudinal length and the extended liner layer distal end comprises a second longitudinal length, wherein a longitudinal length of the proximal liner is the same as the first longitudinal length, and wherein a longitudinal length of the distal liner is the same as the second longitudinal length.

4. The prosthesis of claim 1, wherein the one of the first liner layers immediately adjacent to the expandable tubular frame structure comprises the extended layer.

5. The prosthesis of claim 1, wherein the frame structure is at least one of balloon expandable or self-expanding.

6. A method of making a prosthesis, the method comprising:
    applying a first liner along a luminal side of an expandable tubular frame, the frame including a proximal frame end and a distal frame end, the first liner including a plurality of first liner layers, wherein one of the first liner layers is an extended layer extending longitudinally beyond proximal and distal ends of remaining first liner layers;
    wherein the extended layer comprises an extended liner layer proximal end, an extended liner layer distal end, and an intermediate segment disposed between the extended liner layer proximal and distal ends;
    applying a proximal liner along an abluminal side of the proximal frame end;
    applying a distal liner along the abluminal side of the distal frame end; and bonding the extended liner layer proximal end to the proximal liner along the proximal frame end to define a first bonding site, and bonding the extended liner layer distal end to the distal liner along the distal frame end to define a second bonding site, such that an intermediate region of the frame between the proximal and distal frame ends remains unbonded to the first liner, wherein a non-extended liner layer of one of the remaining first liner layers fails to overlap with the proximal and distal liners.

7. The method of claim 6, wherein a wall thickness of each of the first bonding site and the second bonding site is the same as a wall thickness of the first liner disposed along the intermediate region of the frame.

8. The method of claim 7, wherein the extended liner layer proximal end has a first longitudinal length, the extended liner layer distal end has a second longitudinal length, wherein a longitudinal length of the proximal liner is the same as the first longitudinal length, and wherein a longitudinal length of the distal liner is the same as the second longitudinal length.

9. The method of claim 8, wherein each of the proximal liner and the distal liner comprises multiple layers including a bonding layer disposed in closest proximity to the frame, wherein the extended layer is configured for remaining unbonded to the frame along the intermediate region and configured for bonding to the bonding layer of the proximal and distal liners along the respective bonding sites.

10. The method of claim 9, wherein the bonding step includes heating the bonding sites to at least a melt temperature of the bonding layer of the proximal and distal liners.

11. A prosthesis comprising:
an expandable tubular frame structure having a proximal frame end and a distal frame end;
a covering disposed along the frame structure, the covering including a first liner, a proximal liner, and a distal liner discrete from the proximal liner, the first liner comprising a plurality of first liner layers, wherein at least one of the first liner layers is an extended layer extending beyond a proximal end of remaining first liner layers and a distal end of the remaining first liner layers of the first liner, wherein a proximal end of the extended layer is bonded to the proximal liner along the proximal frame end at a first coupling segment, and a distal end of the extended layer is bonded to the distal liner along the distal frame end at a second coupling segment, wherein one of the first liner layers immediately adjacent to the expandable tubular frame structure remains unbonded to the expandable tubular frame structure along an intermediate region of the frame structure disposed between the proximal and distal frame ends, and wherein the first and second coupling segments have a common wall thickness, and an intermediate segment of the first liner that remains unbonded to the expandable tubular frame structure comprises a wall thickness sized the same as the common wall thickness.

12. The prosthesis of claim 11, wherein the proximal end of the extended layer comprises a first longitudinal length and the distal end of the extended layer comprises a second longitudinal length, wherein a longitudinal length of the proximal liner is the same as the first longitudinal length, and wherein a longitudinal length of the distal liner is the same as the second longitudinal length.

13. The prosthesis of claim 11, wherein the one of the first liner layers immediately adjacent to the expandable tubular frame structure comprises the extended layer.

14. The prosthesis of claim 11, wherein the frame structure is at least one of balloon expandable or self-expanding.

* * * * *